(12) United States Patent
Chuang et al.

(10) Patent No.: US 9,283,172 B2
(45) Date of Patent: *Mar. 15, 2016

(54) USE OF STEM CELL CONDITIONED MEDIUM TO INDUCE ZO-1 PROTEINS EXPRESSION FOR SKIN REGENERATION, REPAIR AND FIRMING

(71) Applicant: GROWGENE BIOTECH INC., Taipei (TW)

(72) Inventors: Pei-Chuan Chuang, Taipei (TW); Huei-Chun Liu, Taipei (TW)

(73) Assignee: Growgene Biotech Inc., Taipei (TW)

( * ) Notice: Subject to any disclaimer, the term of this patent is extended or adjusted under 35 U.S.C. 154(b) by 155 days.

This patent is subject to a terminal disclaimer.

(21) Appl. No.: 14/105,343

(22) Filed: Dec. 13, 2013

(65) Prior Publication Data

US 2015/0164783 A1    Jun. 18, 2015

(51) Int. Cl.
- *A61K 35/50* (2015.01)
- *A61K 35/12* (2015.01)
- *A61K 8/98* (2006.01)
- *A61Q 19/08* (2006.01)

(52) U.S. Cl.
CPC ............... *A61K 8/982* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 4,959,353 A | 9/1990 | Brown et al. | |
| 5,104,977 A | 4/1992 | Sporn et al. | |
| 5,130,298 A | 7/1992 | Cini et al. | |
| 2008/0311093 A1* | 12/2008 | Skinner | 424/93.21 |
| 2009/0136459 A1* | 5/2009 | Wu et al. | 424/93.7 |
| 2010/0143289 A1* | 6/2010 | Cohen et al. | 424/85.1 |
| 2010/0323027 A1* | 12/2010 | Lim et al. | 424/520 |
| 2011/0294731 A1* | 12/2011 | Torfi | 514/7.6 |
| 2012/0141399 A1* | 6/2012 | You et al. | 424/62 |
| 2014/0148915 A1* | 5/2014 | Aljitawi et al. | 623/23.72 |

FOREIGN PATENT DOCUMENTS

TW    201338810 A    10/2013

OTHER PUBLICATIONS

Arno et al. Stem Cell Research & Therapy 2014, 5:28, pp. 1-13.*
Ahn, et al., "FGF2 stimulates the proliferation of human mesenchymal stem cells through the transient activation of JNK signaling"; FEBS letters 583:17, Sep. 3, 2009, pp. 2922-2926.

* cited by examiner

*Primary Examiner* — Chris R Tate
*Assistant Examiner* — Douglas F White
(74) *Attorney, Agent, or Firm* — Rosenberg, Klein & Lee

(57) ABSTRACT

A use of a stem cell conditioned medium to induce ZO-1 proteins expression for skin regeneration, repair and firming is revealed herein. First, mesenchymal stem cells are cultured in a cell culture dish containing complete growth media, wherein the complete growth media include α-MEM, fetal bovine serum, and human-basic fibroblast growth factors. After mesenchymal stem cells are sub-cultured in the complete growth media for three times, a conditioned medium which can effectively increase the activation of tight junction protein Zonula occludens-1 (ZO-1) can be acquired from the basal medium.

2 Claims, 3 Drawing Sheets

USE OF STEM CELL CONDITIONED MEDIUM TO INDUCE ZO-1 PROTEINS EXPRESSION FOR SKIN REGENERATION, REPAIR AND FIRMING

BACKGROUND OF THE INVENTION

1. Field of the Invention

The present invention relates to a use of a stem cell conditioned medium to induce ZO-1 proteins expression for skin regeneration, repair and firming. The conditioned medium obtained from human Wharton's jelly-derived mesenchymal stem cells (WJMSCs) conditioned basal medium can effectively increase the activation of tight junction protein Zonula occludens-1 (ZO-1) in skin cells so as to improve users' undesired skin conditions, e.g. slack skin.

2. Description of Related Art

Due to the increase in life expectancy, how to slow down aging has become one of important issues in medicine. In mammals such as humans, skin is the soft outer covering all over a mammal body and enables to interface with the environment as the first line of defense from external factors. Therefore, skin is the most vulnerable organ to external stimuli and UV damage. Skin reflects the physiological state, mental state as well as the age of individuals. When skin is lack of water, it often leads to aging, rough, loose or wrinkle formation. The young and tight skin, which often presents a shining gloss, usually makes people look spirited. However, with increasing ages, skin may gradually reveal weakness, dullness, wrinkles or sagging owing to the loss of natural moisturizing factors, cells disarrangement, and poor water retention capacity in epithelia. Therefore, in addition to whitening, recently people also focus on the maintenance of skin firmness. In the dermis, there are two important proteins, collagen and elastin, which support skin and make it plump and firm. However, these two proteins will naturally decrease with age, and fibers among cells will be also degraded with time, resulting in the loss of elasticity and firmness of skin.

Nowadays, there are various methods for treating sagging and wrinkling of skin, including laser facelift, injections of Botox, hyaluronic acid or collagen, or supplements with growth factors. For instance, U.S. Pat. No. 4,959,353, issued on 25 Sep. 1990, disclosed a "Promotion of corneal stroma wound healing with human epidermal growth factor prepared from recombinant DNA." It describes the use of epidermal growth factor for treatment of corneal wounds. U.S. Pat. No. 5,130,298, issued on 14 Jul. 1992, disclosed a "Stabilized compositions containing epidermal growth factor." It shows that the compositions containing epidermal growth factors can be used stably against decomposition of the metallic cations for treating wounds. U.S. Pat. No. 5,104,977, issued on 14 Apr. 1992, disclosed a "Purified transforming growth factor beta." It describes the use of the transformation growth factor β (TGF-beta) or transformed cells growth factor α (TGF-alpha) to the treatment of injured tissue. However, protein growth factors cannot be used to reduce the aging of the non-flaking or non-injured skin. In addition, most methods of treating sagging and wrinkling of the skin are expensive and must require experts to conduct treatment. Moreover, patients require a period of time for recovery after the treatment.

In these years, studies of stem cells have been a growing trend in the world. Stem cells can mainly be divided into two categories, embryonic stem cells and adult stem cells. Mesenchymal stem cells (MSCs) belong to adult stem cells and have a great potential for differentiation. MSCs can differentiate into not only tissues (such as skeleton) derived from mesoderm, but also visceral cells (such as liver and pancreas) derived from endoderm and neurons derived from ectoderm. MSCs are ubiquitous in adults' bodies and can be isolated from bone marrows and various organs. However, the number of MSCs in the bodies is small, and adults' MSCs are known to gradually decrease with the age of the donors. Therefore, how to obtain a sufficient amount of MSCs becomes very important. Bone marrow MSCs are mainly derived from adult bone marrow, but invasive ways to get the bone marrow MSCs may cause pain and discomfort to donors. Umbilical cords contain a number of rich and young MSCs with strong differentiation potential, so they can be used as an important source of mesenchymal stem cells. In comparison with obtaining MSCs from bone marrows, obtaining MSCs from umbilical cords is relatively easy. Moreover, recent studies showed that human mesenchymal stein cell-derived conditioned medium (MSC-CM) can enhance corneal endothelial cells proliferation. This conditioned medium can increase expression of tight junction proteins and effectively assist cells in their normal arrangement and growth.

SUMMARY OF THE INVENTION

In view of the above-mentioned problems, the object of the present invention is to provide a use of a stem cell conditioned medium to induce ZO-1 proteins expression for skin regeneration, repair and firming. The conditioned medium acquired from WJMSCs conditioned basal medium can effectively increase the activation of tight junction protein Zonula occludens-1 (ZO-1) in skin cells so as to improve users' undesired skin conditions, e.g. slack skin.

Disclosed herein is a use of a stein cell conditioned medium to induce ZO-1 proteins expression for skin regeneration, repair and finning, wherein the stem cell conditioned medium is manufactured by the steps of (a) culturing stem cells in a cell culture dish containing complete growth media therein, wherein the complete growth media include α-MEM, fetal bovine serum, and human-basic fibroblast growth factors; and (b) sub-culturing stem cells at least for three times (preferably for three times) in the complete growth media.

According to an embodiment of the present invention, the stein cell is mesenchymal stein cell, preferably human Wharton's jelly-derived mesenchymal stein cell.

According to an embodiment of the present invention, the complete growth media include 10-20 wt. % fetal bovine serum, 2-6 ng/ml (preferably 4 ng/ml) human-basic fibroblast growth factors, and the remaining weight percentage of minimum essential medium alpha (α-MEM).

DETAILED DESCRIPTION OF THE PREFERRED EMBODIMENT

Figure 1A:
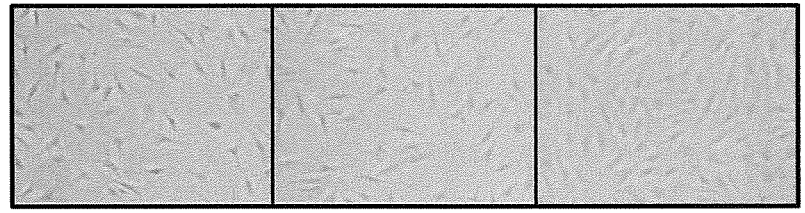
FIG. 1A is a representative diagram showing growth and arrangement of fibroblasts in the basal medium, Hs68-CM and WJMSC-CM.

A use of a stem cell conditioned medium to induce ZO-1 proteins expression for skin regeneration, repair and firming, wherein the stem cell conditioned medium is made by the steps of:

(a) culturing stein cells in a cell culture dish containing complete growth media therein, wherein if the complete growth media is calculated by a total weight percentage of 100%, it comprises 10-20 wt. % (preferably 20 wt. %) fetal bovine serum (FBS), 2-6 ng/ml (preferably 4 ng/ml) human-basic fibroblast growth factors and a remaining weight percentage of α-MEM.

(b) sub-culturing stem cells at least for three times (preferably for three times) in the complete growth media, wherein the stem cells are mesenchymal stern cells, preferably human Wharton's jelly-derived mesenchymal stein cells.

Hereinafter, an exemplary embodiment of the present invention will be described in detail with reference to the accompanying drawings.

Example 1

Compare Cell Density in Fibroblast Conditioned Medium and Stem Cell Conditioned Medium Cell Culture Human foreskin fibroblasts (Hs68: BCRC 603800) were cultured in dishes containing complete growth medium (BD Falcon/BD biosciences) which includes Dulbecco's Modified Eagle Medium (DMEM) (Gibco) supplemented with 10% fetal bovine serum (FBS) (Gibco). Human Wharton's jelly-derived mesenchymal stein cells (WJMSC: BCRC H-WJ001) were cultured in dishes containing complete growth medium (BD Falcon/BD biosciences) which includes DMEM supplemented with 20% FBS and 4 ng/ml human-basic fibroblast growth factor (bFGF) (Peprotech). The Hs68 and the WJMSCs were incubated at 37° C. in 5% $CO_2$ and were sub-cultured after incubation for three days.

In the subculture (cell passaging) experiment, the culture medium (complete growth medium) was removed and the attached cells were rinsed by phosphate buffered saline (PBS) (Roche). After the supernatant was removed, cells were incubated in 0.05% Trypsin-EDTA (Life Technologies) for five minutes, and then the detached cells can be acquired from the dishes. The cells were resuspended in culture medium and centrifuged at 1,200 rpm for 3 min. After the supernatant was removed, cell pellets were resuspended in culture medium and cultured at 37° C. in 5% $CO_2$. Then cells were sub-cultured for three times in the complete growth media.

Preparation of Conditioned Medium

Human foreskin fibroblasts (Hs68) were seeded onto culture dishes at a cell density of $2 \times 10^4$ cells/$cm^2$ and were incubated for one day. Then the attached cells were washed three times with PBS, and the medium was replaced with basal medium (only containing DMEM). After Hs68 were maintained for an additional 48 hours, the basal medium were collected in 50 ml centrifuge tubes and centrifuged at 2,000 rpm for 10 min. Then the supernatant was filtered through a 0.22-µm filtration unit (BD Falcon/BD biosciences) and used as human foreskin fibroblasts conditioned medium (Hs68-CM). The Hs68-CM was stored at −20° C.

Human Wharton's jelly-derived mesenchymal stem cells (WJMSCs) were seeded onto culture dishes at a cell density of $5 \times 10^4$ cells/$cm^2$ and were incubated for one day. Then the attached cells were washed three times with PBS, and the medium was replaced with basal medium (containing DMEM and 4 ng/ml bFGF). After WJMSCs were maintained for an additional 48 hours, the basal medium were collected in 50 ml centrifuge tubes and centrifuged at 2,000 rpm for 10 min. Then the supernatant was filtered through a 0.22-µm filtration unit (BD Falcon/BD biosciences) and used as WJMSC conditioned medium (WJMSC-CM). The WJMSC-CM was stored at −20° C.

Cell Density Analysis

Human foreskin fibroblasts (Hs68) were seeded onto 6-well dishes at a cell density of $2 \times 10^4$ cells/$cm^2$ and were incubated for one day. Then the attached cells were washed three times with PBS. Hs68-basal medium, Hs68-CM, and WJMSC-CM were respectively added to the wells for incubating 72 hours. Three fields from each well were measured by an optical microscope (Leica). In addition, after 72-hour incubation, the attached cells were washed three times with PBS. The supernatant were removed and cells were trypsinized with 0.05% trypsin-EDTA for 5 minutes at 37° C. Then cells were resuspend in culture medium and centrifuged at 1,200 rpm for 3 min. After the supernatant were removed, the remaining cell pellets were resuspend in 0.2 ml PBS and added with 0.2 ml trypan blue (Invitrogen) (PBS: trypan blue=1:1) for staining. Trypan blue exclusion test and hemocytometer were used to calculate the number of cells. The experiments were performed in triplicate.

Example 2

Compare the Effect of Fibroblast Conditioned Medium and Stem Cell Conditioned Medium on ZO-1 Expression Total RNA Extraction and Reverse Transcription Polymerase Chain Reaction (RT-PCR)

Human foreskin fibroblasts (Hs68) were seeded onto culture dishes at a cell density of $2 \times 10^4$ cells/$cm^2$. After incubated for one day, the attached cells were washed three times with PBS. Hs68-basal medium, Hs68-CM, and WJMSC-CM were respectively added to the culture dishes. After the cells were maintained for five days, cells were washed with PBS. Total RNA was extracted by use of the RNA isolation kit (Welgene biotech) according to manufacturer's protocol. Single-strand cDNA was synthesized with 1 µg of total RNA by use of the reverse transcriptase kit (Roche). The cDNA samples were subjected to PCR with specific primers of ZO-1 (Forward: 5'-TTCTGAGGCCTGTAACCATTTT-3' and Backward: 5'-AATTGGATACCACTGGGCATAG-3') and GAPDH (Forward: 5'-GAGATCCCTCCAAAATCAAGTG-3' and Backward: 5'-GAGTCCTTCCACGATACCAAAG-3'). ZO-1 genes were analyzed in comparison with GAPDH as an internal control. PCR reactions were performed as follows: (1) denaturation at 95° C. for 5 minutes, (2) 29 cycles of annealing at 95° C. for 30 seconds, 54° C. for 30 seconds, and 72° C. for 30 seconds, and (3) elongation at 72° C. for 3 minutes. PCR products were separated by electrophoresis on 1.5% agarose gels, containing 10 µg/ml ethidium bromide (EtBr). The gels were detected under ultraviolet illumination (280 nm) by use of CCD image capture system (Alphalmager™).

Example 3

Compare the Effect of Fibroblast Conditioned Medium and Stem Cell Conditioned Medium on Cell Migation Migration Assay Human foreskin fibroblasts (Hs68) were seeded onto 6-well dishes at a cell density of $1 \times 10^5$ cells/$cm^2$. After incubated for one day, the attached cells were washed three times with PBS. Hs68-basal medium, Hs68-CM, and WJMSC-CM were respectively added to the wells. Scrape-wounding of the cells was performed using a plastic pipette tip. Following scraping, the medium containing detached cells was removed and replaced with Hs68-basal medium, Hs68-CM, or WJMSC-CM; cells were further maintained for 24 hours. Cell migration and the recovery to a cell monolayer were determined by an optical microscope (Leica) at different time points. The width of the wound area was measured using ImageJ software (NIH), and three fields from each well were measured.

Results

Figure 1B:
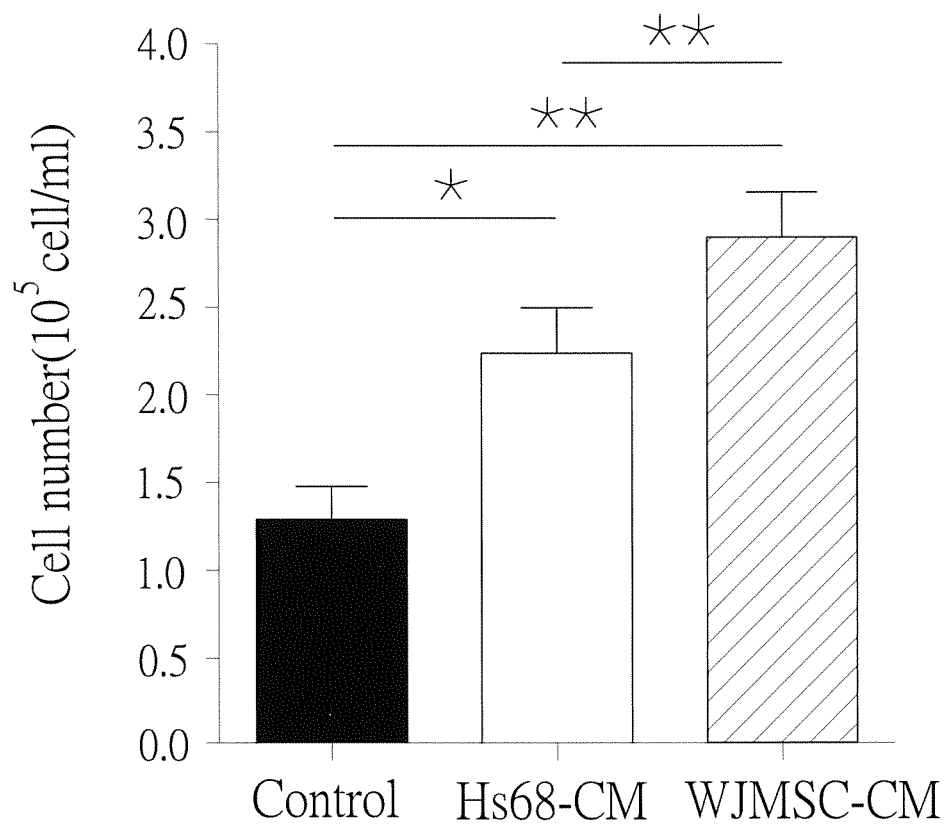
FIG. 1B is a diagram showing that WJMSC-CM increases cell number of Hs68.

Result 1: Stem Cell Conditioned Medium can Effectively Promote Cell Growth and Normal Arrangement of Fibroblasts Referring to FIG. 1A, it is a representative diagram showing cell growth and arrangement of fibroblasts (Hs68) after a three-day incubation in the basal medium (control), fibroblast conditioned medium (Hs68-CM) and stem cell conditioned medium (WJMSC-CM). WJMSC-CM significantly promotes growth rate and arrangement of cells. FIG. 1B is a diagram showing an analysis of cell number in different culture media. The results indicated that Hs68-CM significantly increased 1.76 times the cell number compared with control group by student's t-test analysis. Stem cell conditioned medium (WJMSC-CM) can also increase cell growth rate, which is 2.29 times the cell number of control group. Moreover, WJMSC-CM more significantly accelerates the cell growth rate than does Hs68-CM, which causes a relative tight arrangement of cells. The experiments were performed in triplicate. Results were expressed as mean±SEM. *$P<0.05$, **$P<0.01$.

Result 2: Stem Cell Conditioned Medium can Increase Expression of ZO-1 Genes

Figure 2A:
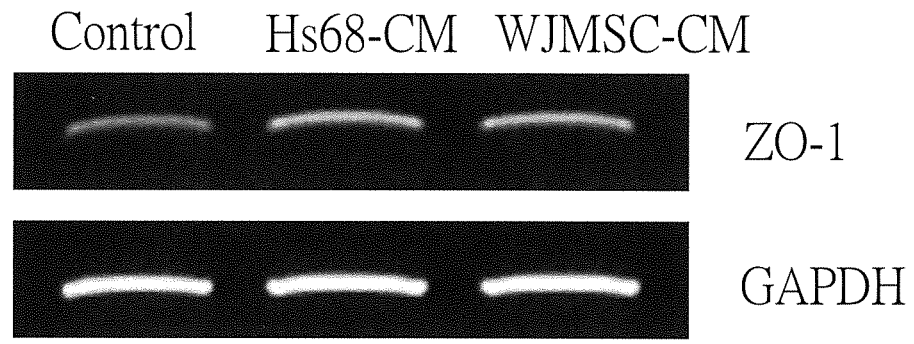
FIG. 2A is a representative diagram showing expression of ZO-1 genes in Hs68 cultured with basal medium, Hs68-CM and WJMSC-CM.

Referring to FIG. 2A, it is a representative diagram showing expression of ZO-1 genes in fibroblasts (Hs68) cultured with basal medium (control), fibroblast conditioned medium (Hs68-CM) and stem cell conditioned medium (WJMSC-CM) for five days. Expression of ZO-1 genes was assessed by RT-PCR.

Figure 2B:
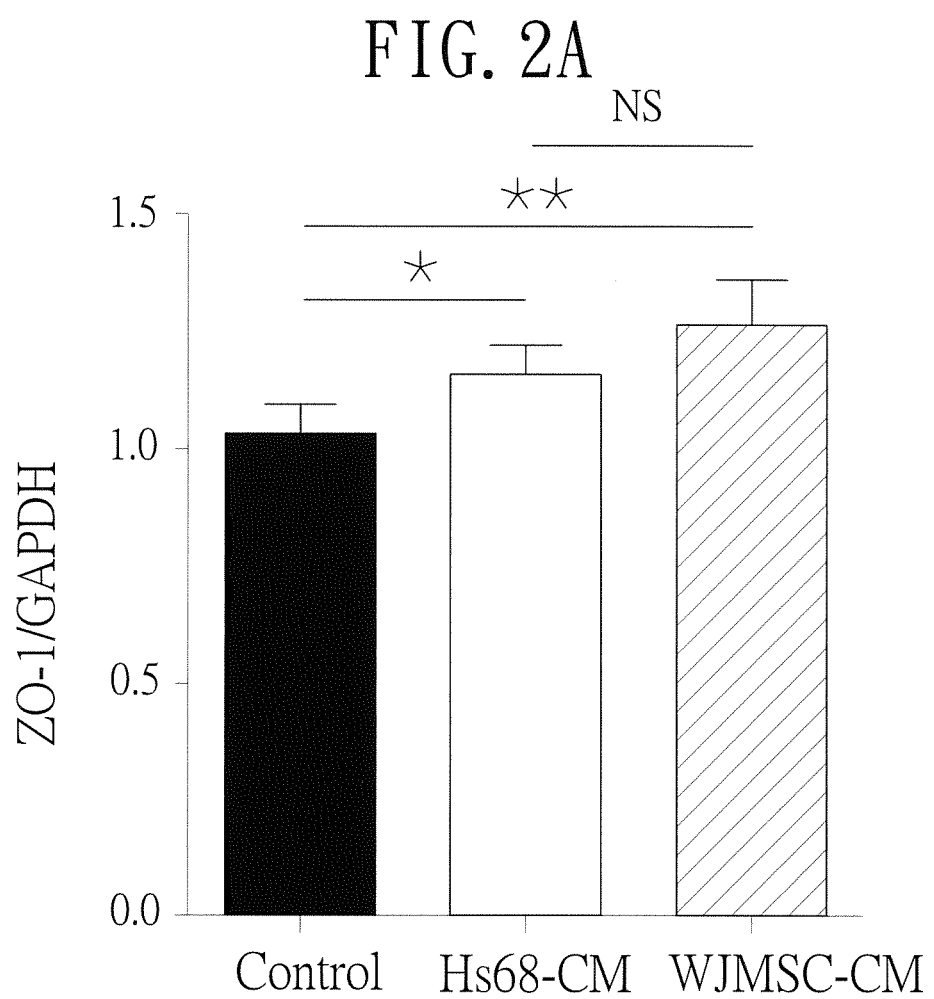
FIG. 2B is a diagram showing that WJMSC-CM increases expression of ZO-1 genes.

Referring to FIG. 2B, by a student's t-test analysis, the result indicates that Hs68-CM and WJMSC-CM can increase ZO-1 expression, which are 1.12 times and 1.24 times the ZO-1 expression level of control group. The experiments were performed in triplicate. Results were expressed as mean±SEM. *$P<0.05$, **$P<0.01$. NS: not significant.

Figure 3A:
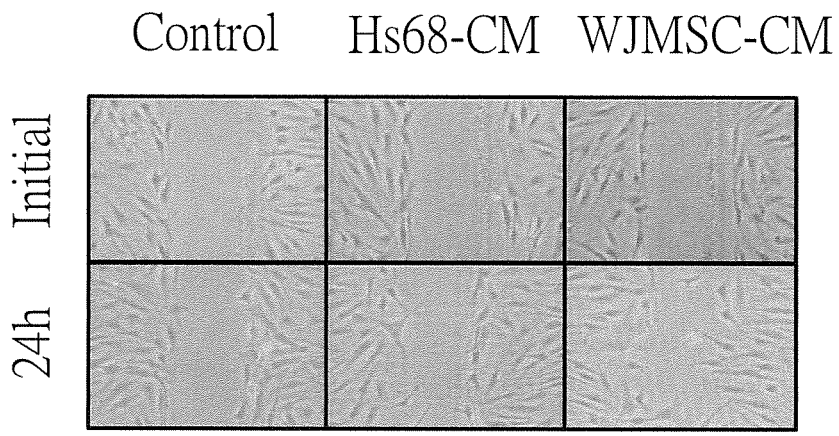
FIG. 3A is a representative diagram showing the effect of basal medium, Hs68-CM and WJMSC-CM on wound healing of Hs68.

Result 3: Stem Cell Conditioned Medium can Effectively Promote Cell Migration for Wound Healing Fibroblasts (Hs68) were cultured with basal medium (control), fibroblast conditioned medium (Hs68-CM) or stem cell conditioned medium (WJMSC-CM), and the monolayer cells were then wounded by using a plastic pipette tip. After 0 (initial) or 24 hours, the remaining wound areas were determined by an optical microscope. As shown in FIG. 3A, a representative diagram showing the effect of basal medium (control), Hs68-CM and WJMSC-CM on wound healing is revealed. Decreased wound remaining area demonstrates that cells have better abilities of movement and wound healing. After cells were incubated in WJMSC-CM for 24 hours, WJMSC-CM significantly promotes cell movement.

Figure 3B:
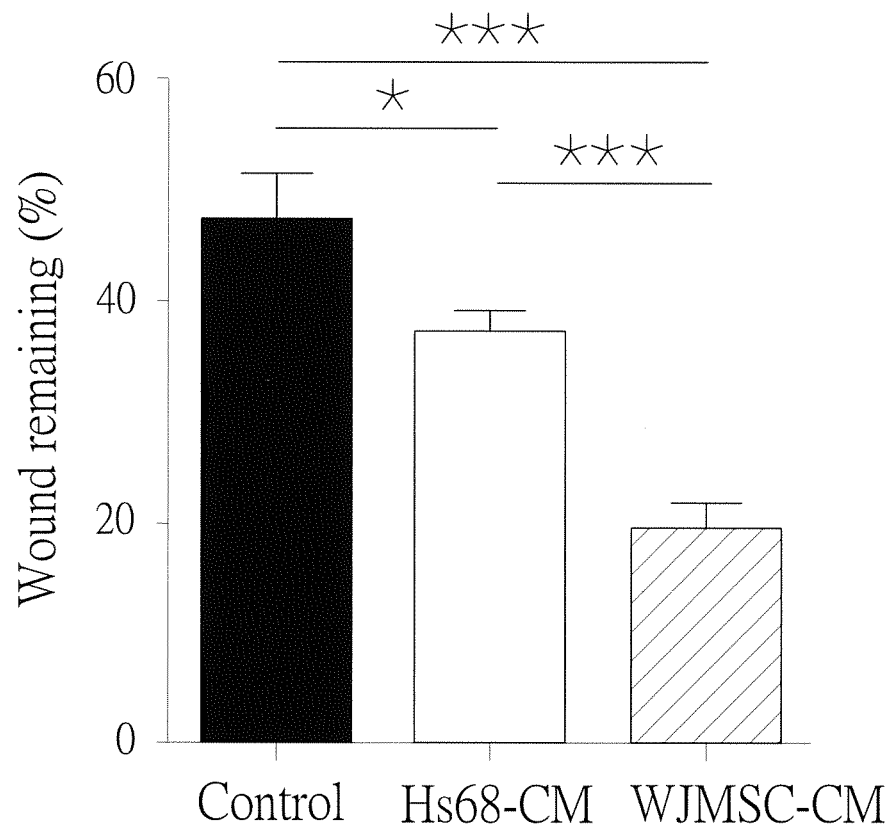
FIG. 3B is a diagram showing that WJMSC-CM effectively promotes wound healing of Hs68.

Referring to FIG. 3B, cells maintained in both Hs68-CM and WJMSC-CM have better abilities of movement and wound healing than cells maintained in basal medium (control). Especially, the results shows that cells maintained in WJMSC-CM for 24 hours have the fastest healing rate. The experiments were performed in triplicate. Results were expressed as mean±SEM. *$P<0.05$, ***$P<0.005$.

To sum up, above results showed that WJMSC-CM promotes not only cell growth as well as normal arrangement, but also ZO-1 expression, cell movement and wound healing. Accordingly, WJMSC-CM can further be used as the material added to the cosmetic composition for improving users' undesired skin conditions, e.g. slack or impaired skin.

According to the above description, in comparison with the traditional technique, a use of a stem cell conditioned medium to induce ZO-1 proteins expression for skin regeneration, repair and firming according to the present invention has the advantages as following:

1. The mesenchymal stem cell conditioned medium (WJMSC-CM) containing a large number of growth factors and interaction proteins can not only stimulate expression of tight junction protein and adhesion molecule, but also increase expression of ZO-1. Therefore, it can be used to promote cell arrangement and maintain elasticity of skin for improving the problems of sagging skin and wrinkles formation.
2. In comparison with obtaining MSCs from bone marrows, Wharton's jelly MSCs can be acquired from newborn babies' unwanted umbilical cords. Therefore, collecting MSCs from umbilical cords may not cause pain to donors and can prevent ethical problems. Moreover, the number of stem cells in umbilical cords is larger than that of other parts in human's bodies, so obtaining MSCs from umbilical cords is relatively easy.
3. In comparison with bone marrows-derived MSCs, Wharton's jelly MSCs belong to the earlier stage cells and can differentiate into much more cell types. Therefore, the conditioned media of Wharton's jelly MSCs, which contains protein factors to enhance ZO-1 expression, can not only promote skin firmness and skin elasticity, but also effectively smooth wrinkles so as to slow down aging.

What is claimed is:

1. A method of firming skin using a stem cell conditioned medium, comprising:
applying an effective amount of the stem cell conditioned medium to the skin of a subject in need thereof so as to induce ZO-1 protein expression thereby firming the skin; and wherein said stem cell conditioned medium is produced by: (a) culturing human Wharton's jelly mesenchymal stem cells in a cell culture dish containing a complete growth medium, wherein the complete growth medium includes α-MEM, fetal bovine serum, and human-basic fibroblast growth factors; and (b) sub-culturing the human Wharton's jelly mesenchymal stem cells in the complete growth medium at least three times and transferring the stem cells to a basal medium to obtain said stem cell conditioned medium, wherein the basal medium includes α-MEM and human-basic fibroblast growth factors.

2. The method of claim 1, wherein the complete growth medium includes about 10 wt. %-20 wt. % of fetal bovine serum, about 2-6 ng/ml of human-basic fibroblast growth factors, and a remaining weight percentage of α-MEM and the basal medium includes about 2-6 ng/ml of human basic fibroblast growth factors and a remaining weight percentage of α-MEM.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: ZO-1 forward primer

<400> SEQUENCE: 1
ttctgaggcc tgtaaccatt tt                                                22
```

```
<210> SEQ ID NO 2
<211> LENGTH: 22
<212> TYPE: DNA
<213> ORGANISM: Artificial Sequence
<220> FEATURE:
<223> OTHER INFORMATION: ZO-1 backward primer

<400> SEQUENCE: 2
aattggatac cactgggcat ag                                            22

<210> SEQ ID NO 3
<211> LENGTH: 22
<212> TYPE: DNA
<213> ORGANISM: Artificial Sequence
<220> FEATURE:
<223> OTHER INFORMATION: GAPDH forward primer

<400> SEQUENCE: 3
gagatccctc caaaatcaag tg                                            22

<210> SEQ ID NO 4
<211> LENGTH: 22
<212> TYPE: DNA
<213> ORGANISM: Artificial Sequence
<220> FEATURE:
<223> OTHER INFORMATION: GAPDH backward primer

<400> SEQUENCE: 4
gagtccttcc acgataccaa ag                                            22
```